(12) United States Patent
Amata et al.

(10) Patent No.: US 7,592,180 B2
(45) Date of Patent: Sep. 22, 2009

(54) METHOD FOR EVALUATING INSULIN RESISTANCE

(75) Inventors: Junichi Amata, Fuchu (JP); Shigeo Takahashi, Shinagawa-ku (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 273 days.

(21) Appl. No.: 11/663,950

(22) PCT Filed: Sep. 28, 2005

(86) PCT No.: PCT/JP2005/017820

§ 371 (c)(1),
(2), (4) Date: Mar. 28, 2007

(87) PCT Pub. No.: WO2006/035804

PCT Pub. Date: Apr. 6, 2006

(65) Prior Publication Data

US 2008/0066526 A1    Mar. 20, 2008

(30) Foreign Application Priority Data

Sep. 28, 2004 (JP) .............................. 2004-281680

(51) Int. Cl.
*G01N 33/48* (2006.01)

(52) U.S. Cl. .............................. 436/63; 436/86; 436/87; 436/94; 530/303

(58) Field of Classification Search .................. 436/63, 436/86, 87, 94, 95; 530/303
See application file for complete search history.

(56) References Cited

U.S. PATENT DOCUMENTS

2006/0073097 A1* 4/2006 Ma et al. ..................... 424/9.1

OTHER PUBLICATIONS

Matsuhisa et al. Diabetes Research and Clinical Practice, vol. 77, 2007, pp. 151-154.*

Minoru Inoue et al., "2-gata Tonyobyo Kanja ni Okeru Adiponectin no Igi", Seibutsu Shiryo Bunseki, vol. 26, No. 2, 2003, pp. 145 to 152, Summary, p.149, Fig. 7.

Toshimasa Yamauchi et al., "Insulin Teikosei Hatsugen no Bunshi Kiko to Sono Hyokaho", Japanese Journal of Clinical Medicine, vol. 62, No. 6, Jun. 2004, pp. 1016 to 1019, 1016 to 1017.

Hotta, Circulating Concentractions of the Adipocyte Protein Adiponectin Are Decreased in Parallel With Reduced Insulin Sensitivity During the Progression to Type 2 Diabetes in Rhesus Monkeys, Diabetes, vol. 50, 2001, pp. 1126 to 1133, summary.

Ono Toshio et al: "The fasting-plasma glucose range in which insulin resistance measured by homeostrasis model assessment correlates with euglycemic clamping" Journal of the Japan Diabetes Society, vol. 42, No. 12, 1999, pp. 1005-1011, XP002477170; ISSN: 021-437X.

Brun J F et al: "Homeostasis model assessment and related simplified evaluations of insulin sensitivity from fasting insulin and glucose." Diabetes Care Jul. 2000, vol. 23, No. 7, Jul. 2000, pp. 1037-1038; XP))2477171; ISSN: 0149-5992.

Yamamoto Y et al: Correlation of the Adipocyte-Derived Protein Adiponectin With Insulin Resistance Index and Serum High-Density Lipoprotein-Cholesterol, Independent of Body Mass Index, In the Japanese Population: Clinical Science, Biochemical Society and the Medical Research Society, London, GB, vol. 103, No. 2, Aug. 2002, pp. 137-142 XP009057476; ISSN: 0143-5221.

Baratta Roberto et al: "Adiponectin relationship with lipid metabolism is independent of body fat mass: Evidence from both cross-sectional and intervention studies" Journal of Clinical Endocrinology & Metabolism, vol. 89, No. 6, Jun. 2004, pp. 2665-2671, XP002477172; ISSN: 0021-972X.

* cited by examiner

*Primary Examiner*—Maureen M Wallenhorst
(74) *Attorney, Agent, or Firm*—Sughrue Mion, PLLC

(57) ABSTRACT

A method for evaluating insulin resistance in a simple and highly reliable manner is provided. This method includes measuring a fasting insulin value in blood, a fasting blood sugar value, and an adiponectin value and evaluating insulin resistance using, as an index, a value obtained by the following calculation formula (I):

$$\text{(Fasting insulin value)} \times \text{(Fasting blood sugar value)} / \text{Adiponectin value} \qquad (I).$$

1 Claim, 1 Drawing Sheet

METHOD FOR EVALUATING INSULIN RESISTANCE

TECHNICAL FIELD

The present invention relates to a method for evaluating insulin resistance, and particularly to a method for evaluating insulin resistance by a new index having a high correlation with a glucose clamp technique.

BACKGROUND ART

An average life expectancy in Japan has reached a world's leading level owing to improvement of life environment and medical advance. However, with rapid aging of the population, percentages of life style-related diseases such as cancers, cardiac diseases, strokes and diabetes in entire diseases are increased, and along with this, the increase of persons in need of nursing care has been a serious social problem.

According to prompt report of diabetes survey results in fiscal Heisei 14 published from Health, Labor and Welfare Ministry in Heisei 15, the persons strongly suspected to have diabetes are 7.40 millions and the persons who can not be denied to have the possibility of diabetes are 8.80 millions, and increased by 500 thousands (6.90 millions in Heisei 9) and 2.00 millions (6.80 millions in Heisei 9), respectively from the same survey carried out in Heisei 9. The diabetes is one of risk factors for cardiac diseases and strokes, and the increase of its candidates indicates that the possibility that the diabetes occurs frequently is high and the risk causing the cardiac diseases and the strokes is high.

In factors such as diabetes, hypertriglyceridemia, HDL hypocholesterolemia and hypertension which compose a metabolic syndrome, insulin resistance is observed to be a common basis, and upstream thereof, accumulation of visceral fat due to excessive eating and shortage of exercise is present. That is, it is very important for early identification to measure the accumulation of visceral fat and the insulin resistance. For measuring the accumulation of visceral fat and the insulin resistance, an abdominal CT examination and a glucose clamp technique are described to be the most reliable methods, respectively. However, these measurements are complicated, and thus, the use thereof is limited in general physicians in practice and medical checkup facilities such as complete health screening.

As an index of the insulin resistance, HOMA (Homeostasis model assessment) is generally used. HOMA has a good correlation with the result of the glucose clamp technique in patients with type 2 diabetes having obesity, but it has been pointed out that its correlativity with the glucose clamp technique is not identified in the non-obese patients with diabetes (see Non-patent literature 1).

Reliability in the evaluation of the insulin resistance by HOMA varies depending on degrees of the obesity (visceral obesity is also involved). Thus, it is difficult that the insulin resistance is correctly evaluated in actual clinical fields, and a highly reliable method which is uniformly applicable for all patients with diabetes has been required.

Non-patent literature 1: "Diabetes" (in Japanese), 42:1005-1010, 1999

DISCLOSURE OF THE INVENTION

Problems to be Solved by the Invention

It is an object of the present invention to provide a method for evaluating insulin resistance in a simple and highly reliable manner.

Means for Solving the Problems

In recent years, insulin sensitizers have been developed and a simple index for the insulin resistance which can be clinically used has been required. HOMA-IR is often used due to its simplicity. However, it has been reported that the correlation of HOMA-IR with the glucose clamp technique is reduced in the cases of blood sugar values of 140 to 170 mg/dL or more and BMI of less than 25 (T. Ono, H. Shiga, Y. Taneda and S. Umemura, For application range of HOMA index —Discussion from relation between insulin resistance and fasting blood sugar value—, Diabetes, 42:1005-11, 1999; T. Yamauchi and T. Kadowaki, Molecular mechanism of insulin resistance expression and its evaluation method, Nippon Rinsho, 62:1016-9, 2004). An attention is required for the application range of HOMA-IR.

As a result of an extensive study to find an index widely applicable for the insulin resistance, the present inventor has found that by dividing a product (i.e., HOMA) of a fasting blood insulin value and a fasting blood sugar value by a blood adiponectin value, an index is obtained which exhibits the high correlation with the glucose clamp technique regardless of an obese degree and a fasting blood sugar level in a patient.

That is, the present invention provides the following method for evaluating the insulin resistance.

A method for evaluating the insulin resistance, wherein a fasting insulin value, a fasting blood sugar value and an adiponectin value in blood are measured and the insulin resistance is evaluated using a value calculated from the following formula (I) as an index:

$$\text{(Fasting insulin value)} \times \text{(Fasting blood sugar value)} / \text{adiponectin value} \qquad (I)$$

The value calculated from the above formula (I) is highly correlated with an M value measured by the glucose clamp technique. Thus, the above measurement value and the M value are parallelized, and using the corresponding M value as a basis, the case with no insulin resistance (normal), the case having the weak insulin resistance and the case having the strong insulin resistance can be evaluated. The higher the value calculated from the formula (I) is, the greater the insulin resistance is. The value calculated from the formula (I) has the negative correlation with the M value, and the smaller the M value is, the larger the value calculated from the formula (I) is.

For example, as one example, when the M value of around 6.6 is made a border (cutoff value) between the normal and the insulin resistance and the M value of around 4.4 is made a border between the weak insulin resistance and the strong insulin resistance, by determining the corresponding value calculated from the formula (I), it is possible to evaluate the insulin resistance with the same reliability as in the M value.

Effects of the Invention

The index obtained from the formula (I) of the present invention is correlated with the result of the glucose clamp technique independently from parameters such as obese degrees and fasting blood sugar values in the patients, and their correlativity is more excellent than that with HOMA even in the obese patients with diabetes.

Therefore, from now, the insulin resistance can be uniformly evaluated without considering the obese degrees in the patients, and it is possible to more easily prevent or treat the diabetes.

BEST MODES FOR CARRYING OUT THE INVENTION

Figure 1:
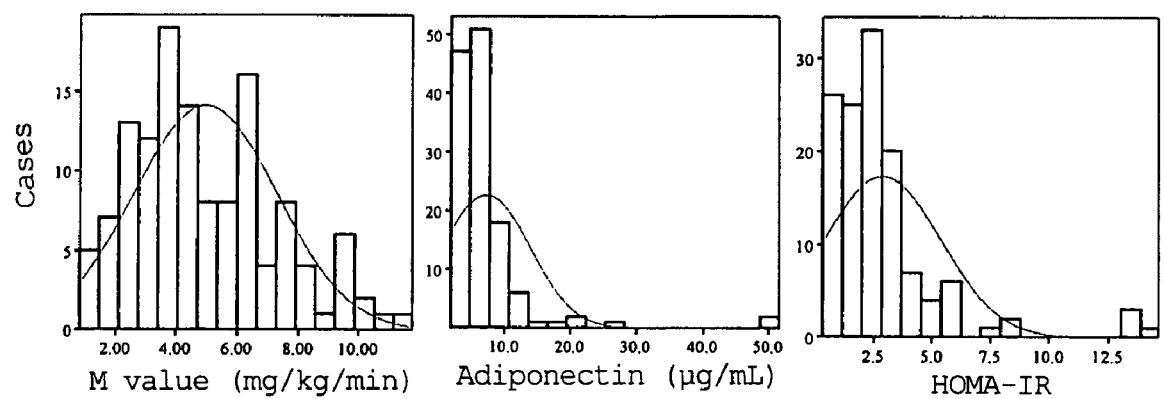
FIG. 1 shows distributions (histograms) of M values, adiponectin concentrations and HOMA-IR.

A fasting insulin value, a fating blood glucose value and an adiponectin value used for the calculation formula of the present invention can be measured in blood (serum or plasma) samples according to standard methods based on publicly known methods such as biological methods (particularly immunological methods) using enzymes and antibodies and optical methods usable for the measurement of the blood sugar value. Examples of respective measurement methods are listed below, but it goes without saying that the measurement methods are not limited thereto.

The method for measuring the insulin concentration includes an EIA method (enzyme immunoassay) and an IRMA (immunoradiometric assay). Generally, the ELA method is frequently used when examined in hospital whereas the IRMA method is often used when the examination is ordered to an outside examination center.

The method for measuring the blood sugar value includes a hexokinase G-6-PDH method, an electrode method and a glucose dehydrogenase method.

As the method for measuring adiponectin, currently an ELISA (enzyme linked immunosorbent assay) method is mainly used, and an RIA (radioimmunoassay) is also used. A human adiponectin measurement kit using latex aggregation as a principle is under clinical trial and can be used.

The new index of the present invention capable of being led from the fasting insulin value, the fasting blood sugar value and the adiponectin value will be described below in comparison with other publicly known indices such as M value (glucose clamp technique) and HOMA.

1. Summary of Study

Making those given the glucose clamp technique the subjects, the correlation of the adiponectin concentration in blood with the M value obtained by the glucose clamp technique is calculated, and the good correlation with a correlation coefficient of 0.462 ($P<0.001$) was obtained. It has been pointed out that HOMA-IR which is the simple index of the insulin resistance reduces the correlation with the M value in the cases of the blood sugar value 140 mg/dL or more and BMI less than 25, and this was also identified in this study. The correlation between the adiponectin concentration and M value was good and had the correlation coefficient of 0.639 ($P<0.001$) even in the cases of BMI less than 22 in which the correlation coefficient between HOMA-IR and the M value was reduced to $-0.287$ ($P=0.138$). Furthermore, the correlation of the "value (hereinafter, blood sugar×IRI/ADN) obtained by dividing the product of the fasting blood sugar value and the fasting insulin concentration by the adiponectin concentration", which was newly invented this time, with the M value was examined. As a result, their correlation was good in the cases in which the correlation of HOMA-IR with the M value was reduced. It was found that their correlation was higher than the correlation of the M value with HOMA-IR in the cases of blood sugar values 140 mg/dL or more and BMI 25 or more and BMI 22 or more in which HOMA-IR exhibited the high correlation. In all of the cases, the correlation coefficient between the blood sugar×IRI/ADN and the M value was $-0.696$ ($p<0.001$) which was higher than the correlation coefficient between HOMA-IR and the M value which was $-0.596$ ($0.001$).

Furthermore, using the M value (logarithmic transformation) as a dependent variable, examination parameters involved in each condition of the blood sugar values of less than 140 mg/dL, 140 mg/dL or more, BMI of less than 25 and 25 or more were calculated by multiple linear regression analysis (stepwise method), and only the blood sugar×IRI/ADN was identified as a common accountable factor.

From the above results, it was demonstrated that the "value obtained by compensating (dividing) the product of multiplying the fasting blood sugar value by the fasting insulin concentration by the adiponectin concentration" could be the new index for the insulin resistance.

2. Selection Criterion

Patients with diabetes aged 20 years or more and less than 70 years, given the glucose clamp technique.

3. Study Method

A fasting venous blood sample was collected once. A gender, a body height, a body weight, a blood pressure, a drug(s) used and the M value of the subjects were surveyed.

As blood biochemical examination parameters, 14 parameters shown in Table 1 and the adiponectin concentration in blood were measured. An adiponectin measurement kit using the latex aggregation as the principle supplied from Mitsubishi Kagaku Yatron Inc. was used for measuring the adiponectin levels, and the values measured in study facilities were used as the other measurement value.

TABLE 1

| Examination Parameter | Type of specimen (Amount) |
| --- | --- |
| Adiponectin | Serum (9 mL) |
| Aspartic acid amino transferase (AST) | |
| Alanine amino transferase (ALT) | |
| γ-Glutamyl transpeptidase | |
| Triglyceride | |
| Total cholesterol | |
| HDL cholesterol | |
| LDL cholesterol | |
| Free fatty acid | |
| Insulin | |
| Urea nitrogen | |
| Creatinine | |
| Uric acid | |
| Blood sugar | Plasma (2 mL) |
| $HbA_1c$ | Whole blood (2 mL) |

4. Selection of Cases Subjected to Analysis

128 Cases (hereinafter the cases given the glucose clamp technique) given the glucose clamp technique were subjected to the analysis.

5. Analysis Method

Since it has been reported that the adiponectin concentration in blood is the index of insulin resistance and is correlated with the M value from the glucose clamp technique (Hotta K, Funahashi T, Bodkin N L, Ortmeyer H K, Arita Y, Hansen B C, et al. Circulating concentrations of the adipocyte protein adiponectin are decreased in parallel with reduced insulin. sensitivity during the progression to type2 diabetes in rhesus monkeys. Diabetes 2001; 50: 1126-3), in the present study, the M values, the adiponectin concentrations in blood and HOMA-IR in 129 cases given the glucose clamp technique were compared. Since HOMA-IR has a problem in its application range, the correlations between the M value and HOMA-IR and between the M value and the adiponectin concentration in blood were examined in the context of the blood sugar values and BMI. Calculation methods of the M value and HOMA-IR are shown below.

M value: a glucose infusion rate controlled to keep the blood sugar at a target concentration by a constant insulin infusion rate is rendered the M value (unit: mg/kg/min).

HOMA-IR: calculated from [fasting blood sugar (mg/dL)]×[fasting insulin (mU/mL)]/405 (unit: none)

Compensation of HOMA-IR Value with Adiponectin Concentration in Blood (New Index of the Present Invention) Including the report by Yamauchi et al. which proved the relation of adiponectin with the insulin resistance, it has reported that adiponectin is involved in the mechanism of increasing the activity of AMP kinase which is the enzyme which facilitates sugar uptake in muscle, and it has also been reported that adiponectin is involved in the mechanism of increasing insulin sensitivity because adiponectin activates a transcription factor (PPARα) involved in regulation of fat burn off to reduce a visceral triglyceride content.

The present inventor has thought that diagnostic accuracy can be enhanced by compensating (dividing) the calculation formula of HOMA-IR with the adiponectin concentration in blood.

Thus, the value obtained by multiplying the fasting blood sugar value by the fasting insulin concentration, which was used for the calculation of HOMA-IR was compensated by dividing this by the adiponectin concentration in blood, and whether the resulting value (hereinafter, blood sugar×IRI/ADN) can be the new index for the insulin resistance was examined.

4. Results

Statistic Amounts and Distributions of M Values, Adiponectin Concentrations and HOMA-IR The statistic amounts and the distributions of the M values, the adiponectin concentrations and HOMA-IR in the cases given the glucose clamp technique are shown in Table 2 and FIG. 1, respectively. Since one result of the fasting insulin level which was required for the calculation of HAMA-IR was fault, the cases of HOMA-IR were 128. As shown in FIG. 1, the distributions of the M values, the adiponectin concentrations and HOMA-IR were shown to be non-normal distributions.

TABLE 2

|  | M value (mg/kg/min) | Adiponectin (μg/mL) | HOMA-IR |
|---|---|---|---|
| Case Number | 128 | 128 | 127 |
| Mean value | 5.0 | 7.1 | 2.9 |
| Median value | 4.6 | 5.5 | 2.3 |
| SD | 2.4 | 6.7 | 2.5 |
| Maximum | 0.8 | 1.9 | 0.3 |
| Minimum | 11.8 | 51.7 | 14.7 |

(a) Correlation of Respective Parameters

Since the cases in which HOMA-IR could be calculated were 127, the correlation of the M value with each parameter was examined in 127 cases. Since non-normality was observed in the distributions of HOMA-IR and the adiponectin concentration in blood, the correlation was calculated using Spearman's rank correlation coefficient (both sides in non-correlation coefficient, significant probability $p<0.05$). The correlation coefficient between the M value and HOMA-IR was $-0.596$ ($p<0.001$) which was the negative correlation. The correlation coefficient between the M value and the adiponectin concentration in blood was $0.463$ ($p<0.001$) which was the positive correlation. The correlation coefficient between the M value and the blood sugar×IRI/ADN was $-0.696$ ($p<0.001$) which was the negative correlation. The significant correlation was obtained in all combination examined, and the combination with the blood sugar×IRI/ADN exhibited the highest correlation.

(b) Examination in the Context of Blood Sugar Values

It is known that the correlation between the M value and HOMA-IR is reduced when the fasting blood sugar level is increased to the level higher than the certain level. This is to be because the elevation of insulin level when the fasting blood sugar is increased is conversely reduced when the blood sugar value is 140 to 170 mg/dL or more. This is attributed to the converse reduction of the insulin level. Thus, by dividing the cases given the glucose clamp technique into a blood sugar value 140 mg/dL or more group and a less than 140 mg/dL group, the correlation of the M value with HOMA-IR, the adiponectin level or the blood sugar×IRI/ADN was examined.

As shown in Table 3, the correlation coefficient between the M value and HOMA-IR was $-0.539$ ($p=0.002$) in the cases of the blood sugar values 140 mg/dL or more whereas $-0.613$ ($p<0.001$) in the cases of blood sugar values less than 140 mg/dL. As have been reported, the correlation coefficient between the M value and HOMA-IR was reduced when the blood sugar value became 140 mg/dL or more. The correlation coefficient between the M value and the adiponectin level was slightly reduced in the cases of the blood sugar values 140 mg/dL or more compared with that in all of the cases. The correlation coefficient between the M value and the blood sugar×IRI/ADN was also reduced in the cases of the blood sugar values 140 mg/dL or more, but was $-0.584$ ($p=0.001$) which was the highest among three parameters. The correlation coefficient between the M value and the blood sugar× IRI/ADN in the cases of blood sugar values less than 140 mg/dL was $-0.734$ ($p<0.001$) which was high.

TABLE 3

Correlation of M value with HOMA-IR, adiponectin level or the blood sugar × IRI/ADN (blood sugar values <140 mg/dL, ≧140 mg/dL)

|  | Total n = 127 | | Blood sugar value <140 mg/dL n = 96 | | Blood sugar value ≧140 mg/dL n = 31 | |
|---|---|---|---|---|---|---|
|  | Correlation coefficient | P value | Correlation coefficient | P value | Correlation coefficient | P value |
| HOMA-IR | −0.596 | <0.001 | −0.613 | <0.001 | −0.539 | 0.002 |
| Adiponectin | 0.463 | <0.001 | 0.482 | <0.001 | 0.433 | 0.015 |
| Blood sugar × IRI/AND | −0.696 | <0.001 | −0.734 | <0.001 | −0.584 | 0.001 |

Correlation coefficient Spearman, significant probability $p < 0.05$ (c) Examination in the Context of BMI A proportional relation between the fasting blood sugar level and fasting insulin level is reduced when the blood sugar level becomes 140 to 170 mg/dL or more. It is known that this relation is shifted to the higher blood sugar level in the obesity compared with the non-obesity. It is also known that the correlation between the M value and HOMA-IR is reduced when BMI becomes less than 25.

Thus, by dividing the cases into a BMI less than 25 group and a BMI 25 or more group, and further dividing into a BMI less than 22 and a BMI 22 or more which is the criterion of a standard body weight in Japanese Society for the Study of Obesity, the correlation of the M value with HOMA-IR, the adiponectin level or the blood sugar×IRI/ADN was examined. The results obtained when BMI was divided at 25 are shown in Table 4. The correlation coefficient between the M value and HOMA-IR was lower in the cases of BMI less than 25 than in the cases of BMI 25 or more as reported, but the correlation with the adiponectin concentration in blood or with the blood sugar×IRI/ADN did not have such a tendency. The correlation coefficient of the blood sugar×IRI/ADN with the M value was −0.607 ($p<0.001$) in the cases of BMI less than 25 and −0.558 ($p<0.001$) in the cases of BMI 25 or more, which were the highest in the three parameters examined.

Subsequently, the results obtained by dividing BMI at 22 are shown in FIG. 5. The correlation coefficient between the M value and HOMA-IR was −0.287 ($p=0.138$) in the cases of BMI less than 22, and was lower than that in all of the cases. However, the correlation coefficient between the M value and the adiponectin concentration in blood was 0.639 ($p<0.01$), and better than that in all of the cases. However, it was 0.303 ($p=0.002$) in the cases of BMI 22 or more and was the lower value. Meanwhile, the correlation coefficient between the M value and the blood sugar×IRI/ADN was −0.584 ($p=0.001$) in the cases of BMI less than 22 and lower than the correlation coefficient of −0.696 ($p<0.001$) in all of the cases. It was −0.650 ($p<0.001$) in the cases of BMI 22 or more. All values from the blood sugar×IRI/ADN were higher than those from HOMA-IR.

TABLE 4

Correlation of M value with HOMA-IR, adiponectin level or the blood sugar × IRI/ADN (BMI <25, ≧25)

|  | Total n = 127 | | BMI <25 n = 62 | | BMI ≧25 n = 65 | |
| --- | --- | --- | --- | --- | --- | --- |
|  | Correlation coefficient | P value | Correlation coefficient | P value | Correlation coefficient | P value |
| HOMA-IR | −0.596 | <0.001 | −0.474 | <0.001 | −0.498 | <0.001 |
| Adiponectin | 0.463 | <0.001 | 0.352 | 0.005 | 0.332 | 0.006 |
| Blood sugar × IRI/AND | −0.696 | <0.001 | −0.607 | <0.001 | −0.558 | <0.001 |

Correlation coefficient Spearman, significant probability $p < 0.05$

TABLE 5

Correlation of M value with HOMA-IR, adiponectin level or the blood sugar × IRI/ADN (BMI <22, ≧22)

|  | Total n = 127 | | BMI <22 n = 28 | | BMI ≧22 n = 99 | |
| --- | --- | --- | --- | --- | --- | --- |
|  | Correlation coefficient | P value | Correlation coefficient | P value | Correlation coefficient | P value |
| HOMA-IR | −0.596 | <0.001 | −0.287 | 0.138 | −0.617 | <0.001 |
| Adiponectin | 0.463 | <0.001 | 0.639 | <0.001 | 0.303 | 0.002 |
| Blood sugar × IRI/AND | −0.696 | <0.001 | −0.584 | 0.001 | −0.650 | <0.001 |

Correlation coefficient Spearman, significant probability $p < 0.05$ (d) Correlation of other Evaluation Parameters with M Value The correlations (Spearman) of the other evaluation parameters obtained in this study with the M value are shown in Table 6.

The highest negative correlation coefficient of −0.509 ($p<0.001$) was observed with the fasting insulin level. Significant negative correlations were observed with BMI (correlation coefficient: −0.499), ALT (−0.421), AST (−0.413), triglyceride (−0.394), the fasting blood sugar level (−0.318) and γ-GTP (−0.287). The significant positive correlation was observed with HDL cholesterol (0.207).

TABLE 6

Correlations of other evaluation parameters with M value

| Examination parameter (case number) | Correlation coefficient with M value (Spearman) | P value |
| --- | --- | --- |
| Blood sugar × IRI/ADN (127) | −0.696 | <0.001 |
| HOMA-IR (127) | −0.596 | <0.001 |
| Insulin (127) | −0.509 | <0.001 |
| BMI (128) | −0.499 | <0.001 |
| Adiponectin (128) | 0.463 | <0.001 |
| ALT (85) | −0.421 | <0.001 |
| AST (85) | −0.413 | <0.001 |
| Triglyceride (126) | −0.394 | <0.001 |
| Blood sugar (128) | −0.318 | <0.001 |
| γ-GTP (83) | −0.287 | 0.008 |

TABLE 6-continued

Correlations of other evaluation parameters with M value

| Examination parameter (case number) | Correlation coefficient with M value (Spearman) | P value |
|---|---|---|
| HDL cholesterol (121) | 0.207 | 0.023 |
| LDL cholesterol (53) | −0.203 | 0.146 |
| Free fatty acid (91) | −0.169 | 0.108 |
| HbA$_1$c (116) | −0.165 | 0.076 |
| Systolic blood pressure (128) | −0.157 | 0.078 |
| Creatinine (128) | 0.121 | 0.175 |
| Urea nitrogen (85) | 0.109 | 0.319 |
| Diastolic blood pressure (128) | −0.091 | 0.304 |
| Uric acid (128) | 0.026 | 0.774 |
| Total cholesterol (127) | 0.008 | 0.925 |

Significant probability p < 0.05

(e) Relation of M Value (Multiple Linear Regression Analysis)

The multiple linear regression analysis (stepwise method) was performed using parameters, i.e., blood sugar, insulin, BMI, triglyceride and HDL cholesterol which exhibited the absolute correlation coefficient of 0.2 or more with M value in 100 or more cases in the above (d) in addition to the adiponectin concentration in blood, HOMA-IR and the blood sugar× IRI/ADN as accountable variables and using the M value as the dependent variable. As a result, in all of the cases subjected, the blood sugar×IRI/ADN, the blood sugar level and the adiponectin concentration were identified as the accountable factors of the M value (Table 7).

The same analysis was performed in the cases divided into the blood sugar values less than 140 mg/dL, more than 140 mg/dL, BMI less than 25 and BMI more than 25. As a result, only the blood sugar×IRI/ADN was identified as the common accountable factor of the M value (Tables 7 and 8)

TABLE 7

Accountable factors of M value (Blood sugar <140 mg/dL, ≧140 mg/dL)

| Evaluation parameters | All cases n = 127 | | Blood sugar <140 (mg/dL) n = 96 | | Blood sugar ≧140 (mg/dL) n = 31 | |
|---|---|---|---|---|---|---|
| | r | P | r | P | r | P |
| Determination coefficient (r$^2$) | 0.366 | | 0.344 | | 0.220 | |
| Blood sugar × IRI/ADN | −0.282 | 0.004 | −0.290 | 0.012 | −0.496 | 0.005 |
| Blood sugar | −0.280 | <0.001 | −0.320 | 0.001 | NA | NA |
| BMI | −0.188 | 0.036 | −0.279 | 0.016 | NA | NA |
| Adiponectin | 0.179 | 0.028 | NA | NA | NA | NA |
| HOMA-IR | NA | | NA | | NA | |
| Insulin | NA | | NA | | NA | |
| Triglyceride | NA | | NA | | NA | |
| HDL cholesterol | NA | | NA | | NA | |

Multiple linear regression analysis (stepwise method)
(Addition: Probability of F value ≦0.05; Elimination: Probability of F value ≧0.10)
Dependent variable: Log (M value), NA: Not accepted

TABLE 8

Accountable factors of M value (BMI <25, ≧25)

| Evaluation parameters | BMI <25 n = 62 | | BMI ≧25 n = 65 | |
|---|---|---|---|---|
| | r | P | r | P |
| Determination coefficient (r$^2$) | 0.449 | | 0.215 | |
| Blood sugar × IRI/ADN | −0.677 | <0.001 | −0.340 | 0.004 |
| Blood sugar | NA | | −0.292 | 0.013 |
| BMI | NA | | NA | |
| Adiponectin | NA | | NA | |
| HOMA-IR | NA | | NA | |
| Insulin | NA | | NA | |
| Triglyceride | NA | | NA | |
| HDL cholesterol | NA | | NA | |

Multiple linear regression analysis (stepwise method)
(Addition: Probability of F value ≦0.05; Elimination: Probability of F value ≧0.10)
Dependent variable: Log (M value), NA: Not accepted 7. Summary Evaluation as Index for Insulin Resistance 1) For the cases of the fasting blood sugar level of 140 mg/dL or more reported that the correlation between the M value and HOMA-IR is reduced, this was examined to confirm its reproducibility. As a result, the correlation coefficient in the cases of the fasting blood sugar level of 140 mg/dL or more was −0.539 (p=0.002) whereas that in the all cases was −0.596(p<0.001), confirming the reduction of the correlation coefficient.

2) Similarly to the blood sugar values, for the cases of BMI of less than 25 also reported that the correlation between the M value and HOMA-IR is reduced, this was examined to confirm its reproducibility. As a result, the correlation coefficient was −0.474 (p<0.001), confirming the reduction of the correlation coefficient. This tendency became remarkable in the cases of BMI of less than 22, and the correlation coefficient was reduced to −0.287 (p=0.138).

3) The correlation of the M value with the adiponectin concentration was compared with the correlation between the M value and HOMA-IR. In the all cases, the correlation coefficient was 0.463 (p<0.001) which was lower than that with HOMA-IR, but in the cases of BMI of less than 22, the correlation coefficient was 0.639 (p<0.001) which was higher than that with HOMA-IR.

4) Considering the action of adiponectin, the value (blood sugar×IRI/ADN) obtained by compensating (dividing) the product (basis of HOMA-IR calculation) of multiplying the fasting blood sugar value by the fasting insulin concentration by the adiponectin concentration was calculated. In the all cases, its correlation coefficient with the M value was −0.696 (p<0.001) which was good and about 0.1 higher as the absolute value than that of HOMA-IR with the M value.

5) In the cases of the blood sugar values of 140 mg/dL or more, BMI of less than 25 or BMI of less than 22 in which the correlation between the M value and HOMA-IR was reduced, the correlation coefficient between the M value and the blood sugar×IRI/ADN was −0.584 (p=0.001), −0.607 (p<0.001) or −0.584 (P=0.001), respectively, which was the good correlation.

6) In the cases of fasting blood glucose values of less than 140 mg/dL (−0.623, p<0.001), BMI of 25 or more (0.498, p<0.001) or BMI of 22 or more (−0.617, p<0.001) in which the M value and HOMA-IR exhibited the good correlation, the correlation coefficient between the M value and the blood sugar×IRI/ADN was −0.734 (p<0.001), −0.558 (p<0.001) or −0.650 (p<0.001) which were all higher than that of HOMA-IR with the M value.

7) The multiple linear regression analysis (stepwise method) was performed for related parameters under the condition of blood sugar values of less than 140 mg/dL, 140 mg/dL or more, BMI of less than 25 or BMI of 25 or more using the M value (logarithmic transformation) as the dependent variable. As a result, only the blood sugar×IRI/ADN was identified as the common accountable factor.

As in the above results, the adiponectin concentration in blood and the blood sugar×IRI/ADN newly invented exhibited the good correlation in the relation with the M value in the range in which HOMA-IR was not applied. In addition, the correlation between the M value and the blood sugar×IRI/ADN was higher than that between the M value and HOMA-IR in the range in which HOMA-IR exhibited the good correlation. Thus it has been demonstrated that the adiponectin concentration in blood and the blood sugar×IRI/ADN are simple indices for evaluating the insulin resistance.

The invention claimed is:

1. A method for evaluating insulin resistance, wherein a fasting insulin value, a fasting blood sugar value and an adiponectin value in blood are measured, and the insulin resistance is evaluated using a value calculated from the following formula (I) as an index:

$$\text{(Fasting insulin value)} \times \text{(Fasting blood sugar value)} / \text{Adiponectin value} \quad \text{(I)}.$$

* * * * *